(12) United States Patent
Cheng et al.

(10) Patent No.: US 10,436,795 B2
(45) Date of Patent: Oct. 8, 2019

(54) CARBON-DETECTED NMR FOR MAPPING BINDING SITES IN INTRINSICALLY DISORDERED REGIONS OF A PROTEIN

(71) Applicant: Institute for Cancer Research, Philadelphia, PA (US)

(72) Inventors: Hong Cheng, Philadelphia, PA (US); Heinrich Roder, Philadelphia, PA (US)

(73) Assignee: Institute For Cancer Research, Philadelphia, PA (US)

(*) Notice: Subject to any disclaimer, the term of this patent is extended or adjusted under 35 U.S.C. 154(b) by 80 days.

(21) Appl. No.: 15/704,852

(22) Filed: Sep. 14, 2017

(65) Prior Publication Data

US 2018/0080942 A1    Mar. 22, 2018

Related U.S. Application Data

(60) Provisional application No. 62/395,604, filed on Sep. 16, 2016.

(51) Int. Cl.

| | | |
|---|---|---|
| *G01N 33/00* | (2006.01) | |
| *G01N 25/18* | (2006.01) | |
| *G01N 33/53* | (2006.01) | |
| *G01N 35/00* | (2006.01) | |
| *G01N 33/48* | (2006.01) | |
| *G01N 33/68* | (2006.01) | |
| *G01N 24/08* | (2006.01) | |

(52) U.S. Cl.
CPC ....... *G01N 33/6854* (2013.01); *G01N 24/088* (2013.01)

(58) Field of Classification Search
CPC ........ G01N 33/00; G01N 25/18; G01N 33/53; G01N 35/00; G01N 33/48
USPC ............ 436/43, 63, 64, 86, 89, 90, 149, 806
See application file for complete search history.

(56) References Cited

U.S. PATENT DOCUMENTS

| | | | |
|---|---|---|---|
| 6,582,910 B1* | 6/2003 | Lam ........................ | C12N 9/90 435/243 |
| 2002/0155463 A1* | 10/2002 | Sun ........................ | C07K 14/47 435/6.14 |
| 2005/0075488 A1* | 4/2005 | Bright .................. | C07K 16/245 530/388.15 |
| 2009/0221691 A1* | 9/2009 | Smrcka .............. | G01N 33/6872 514/454 |
| 2016/0140326 A1* | 5/2016 | Karthikeyan .......... | G16C 20/20 703/1 |
| 2019/0048093 A1* | 2/2019 | Gauthier ............ | C07K 16/2803 |

\* cited by examiner

*Primary Examiner* — Brian J. Sines
(74) *Attorney, Agent, or Firm* — Stradley Ronon Stevens & Young, LLP

(57) ABSTRACT

Carbon-detected NMR is well-suited for mapping binding sites in intrinsically disordered regions of a polypeptides, and for mapping of binding motifs in intrinsically disordered regions with single-residue resolution. Provided are methods of carbon-detected NMR for determining the amino acids that mediate the interaction between an intrinsically disordered polypeptide or protein, or an intrinsically disordered region of a polypeptide, and a biomolecule such as another polypeptide or a nucleic acid.

15 Claims, 9 Drawing Sheets

Specification includes a Sequence Listing.

A.

MDRSKENCIS GPVKATAPVG GPKRVLVTQQ FPCQNPLPVN SGQAQRVLCP
SNSSQRIPLQ AQKLVSSHKP VQNQKQLQ ATSVPHPVSR PLNNTQKSKQ
PLPSAPENNP EELASKQKNE ESKKRQWALE (SEQ ID NO: 5)

Fig. 2A

Red: N-term AURKA
Cyan: N-term AURKA:Apo-CCam=1:0.182

A.

HLWCSNKKNA AVMDQEPAGN RTANSEDSDE QDPEEVTYAQ LDHCVFTQRK ITRPSQRPKT PPTDTILYTE LPNAKPRSKV (SEQ ID NO: 6)

Fig. 4A

SEQUENCE LISTING

```
<160> NUMBER OF SEQ ID NOS: 8

<210> SEQ ID NO 1
<211> LENGTH: 7
<212> TYPE: PRT
<213> ORGANISM: Artificial sequence
<220> FEATURE:
<223> OTHER INFORMATION: N.terminal sequence

<400> SEQUENCE: 1

Gly Pro Gly Tyr Gln Asp Pro
1               5

<210> SEQ ID NO 2
<211> LENGTH: 33
<212> TYPE: PRT
<213> ORGANISM: Artificial sequence
<220> FEATURE:
<223> OTHER INFORMATION: thrombin cleavage/purified C.3DL1/N.terminus

<400> SEQUENCE: 2

Gly Ser Gly Met Lys Glu Thr Ala Ala Ala Lys Phe Glu Arg Gln His
1               5                   10                  15

Met Asp Ser Pro Asp Leu Gly Thr Asp Asp Asp Lys Ala Met Glu
            20                  25                  30

Phe

<210> SEQ ID NO 3
<211> LENGTH: 5
<212> TYPE: PRT
<213> ORGANISM: Artificial sequence
<220> FEATURE:
```

<223> OTHER INFORMATION: SH2 binding motif

<400> SEQUENCE: 3

Glu Glu Val Thr Tyr
1               5

<210> SEQ ID NO 4
<211> LENGTH: 13
<212> TYPE: PRT
<213> ORGANISM: Artificial sequence
<220> FEATURE:
<223> OTHER INFORMATION: Primary SH2 binding motif

<400> SEQUENCE: 4

Glu Glu Val Thr Tyr Ala Gln Leu Asp His Cys Val Phe
1               5                  10

<210> SEQ ID NO 5
<211> LENGTH: 131
<212> TYPE: PRT
<213> ORGANISM: Artificial sequence
<220> FEATURE:
<223> OTHER INFORMATION: N.terminal regulatory region of AurA

<400> SEQUENCE: 5

Met Asp Arg Ser Lys Glu Asn Ile Cys Ser Gly Pro Val Lys Ala Thr
1               5                   10                  15

Ala Pro Val Gly Gly Pro Lys Arg Val Leu Val Thr Gln Gln Phe Pro
            20                  25                  30

Cys Gln Asn Pro Leu Pro Val Asn Ser Gly Gln Ala Gln Arg Val Leu
        35                  40                  45

Cys Pro Ser Asn Ser Ser Gln Arg Ile Pro Leu Gln Ala Gln Lys Leu
    50                  55                  60

Val Ser Ser His Lys Pro Val Gln Asn Gln Lys Gln Lys Gln Leu Gln
65                  70                  75                  80

Ala Thr Ser Val Pro His Pro Val Ser Arg Pro Leu Asn Asn Thr Gln
                85                  90                  95

Lys Ser Lys Gln Pro Leu Pro Ser Ala Pro Glu Asn Asn Pro Glu Glu
            100                 105                 110

Leu Ala Ala Ser Lys Gln Lys Asn Glu Glu Ser Lys Lys Arg Gln Trp
        115                 120                 125

Ala Leu Glu
    130

<210> SEQ ID NO 6
<211> LENGTH: 80
<212> TYPE: PRT
<213> ORGANISM: Artificial sequence
<220> FEATURE:
<223> OTHER INFORMATION: C.3DL1/residues 340.423

<400> SEQUENCE: 6

His Leu Trp Cys Ser Asn Lys Lys Asn Ala Ala Val Met Asp Gln Glu
1               5                   10                  15

Pro Ala Gly Asn Arg Thr Ala Asn Ser Glu Asp Ser Asp Glu Gln Asp
            20                  25                  30

Pro Glu Glu Val Thr Tyr Ala Gln Leu Asp His Cys Val Phe Thr Gln
        35                  40                  45

Arg Lys Ile Thr Arg Pro Ser Gln Arg Pro Lys Thr Pro Pro Thr Asp
    50                  55                  60

```
Thr Ile Leu Tyr Thr Glu Leu Pro Asn Ala Lys Pro Arg Ser Lys Val
65                  70                  75                  80

<210> SEQ ID NO 7
<211> LENGTH: 7
<212> TYPE: PRT
<213> ORGANISM: Artificial sequence
<220> FEATURE:
<223> OTHER INFORMATION: SH2.domain binding motif 1

<400> SEQUENCE: 7

Val Thr Tyr Ala Gln Leu Asp
1               5

<210> SEQ ID NO 8
<211> LENGTH: 6
<212> TYPE: PRT
<213> ORGANISM: Artificial sequence
<220> FEATURE:
<223> OTHER INFORMATION: SH2.domain binding motif 2

<400> SEQUENCE: 8

Ile Leu Tyr Thr Glu Leu
1               5
```

CARBON-DETECTED NMR FOR MAPPING BINDING SITES IN INTRINSICALLY DISORDERED REGIONS OF A PROTEIN

REFERENCE TO GOVERNMENT GRANTS

This invention was made with government support under Grant No. GM056250 awarded by the National Institutes of Health and under Grant No. MCB1412378 awarded by the National Science Foundation. The government has certain rights in the invention.

FIELD

The present disclosure relates generally to the field of protein biochemistry. More particularly, the present disclosure relates to methods for determining the amino acids within intrinsically disordered regions of a protein that contribute to the interaction with amino acids in another protein.

BACKGROUND

Until recently, it was widely believed that a protein must have a well-defined three dimensional (3D) structure to support its function. For example, the specific binding between an enzyme and its substrate has traditionally been explained using a "lock and key" analogy where only the correctly sized "key" (substrate) fits into the "key hole" (active site) of the lock (enzyme). More recently, a growing number of studies have found that many proteins or regions of proteins are inherently flexible and do not conform to the traditional views of protein structure and function. Such an intrinsically disordered protein (IDP) or region of a protein (IDR) does not necessarily have to assume a unique structure to be biologically active, although some become structured when bound to an interaction partner. In fact, the occurrence of unstructured regions under physiological conditions is common in biologically active proteins. Some estimates suggest that as many as half of all eukaryotic proteins contain long (≥40 residues) disordered regions. IDPs have important biological functions and are involved in numerous processes, including regulation of transcription and translation, cellular signal transduction, molecular recognition, and cell cycle regulation, and many have been associated with a wide range of diseases, such as cancer, neurodegeneration, and diabetes. For example, it has been shown that about 80% of human cancer-associated proteins contain predicted regions of disorder of 30 residues or longer.

Because of their plasticity and conformational adaptability, many IDRs/IDPs are capable of interacting with specific proteins or nucleic acids through sequence motifs. The protein interaction of IDRs, which often are rich in serine, threonine, tyrosine and lysine residues, can be tightly and reversibly regulated by covalent posttranslational modification, such as phosphorylation, acetylation or methylation, and ubiquitination.

The mechanism of IDR-mediated protein-protein interactions is poorly understood because of a lack of information on their structural preferences and dynamic properties at atomic resolution. Due to their inherent dynamics, IDRs are not amenable to structure determination by techniques such as x-ray crystallography and conventional NMR, which require a uniquely folded conformation. These regions are often either removed from expression constructs or proteolytically cleaved prior to generation of crystals for structure determination. Therefore, the binding motifs in their sequences are usually not characterized by using x-ray crystallography. NMR spectroscopy is an alternate way to study the structure and function of protein with residue specific resolution. Conventional NMR techniques used in structural biology are based on observation of protons ($^1H$) or indirect detection of the weaker signals from carbon ($^{13}C$) or nitrogen ($^{15}N$) isotopes via protons, which can be detected with much higher sensitivity than hetero-nuclei.

The quality of NMR spectra of IDRs/IDPs is often poor because they exist as dynamic ensembles of conformations under physiological conditions of pH and salinity, in the presence or absence of binding partners. This is schematically illustrated in FIGS. 1A and 1B, which show the effect of conformational exchange between different states, such as bound/closed (panel a) and unbound/open (panel b) states on a simple NMR spectrum (see, FIG. 1A). In the presence of conformational exchange, the line-width of an NMR signal depends not only on the transverse relaxation rates (R2) of a nucleus in each state, but also on the relative magnitudes of exchange rate ($k_{ex}$) and the frequency separation (chemical shift) between the NMR signals of the two states (see, FIG. 1B).

The NMR signal will be broad and difficult to detect when the exchange rate equals or is close to the frequency difference (Δv) between the states (intermediate exchange) (see, FIG. 1B). The line broadening effect is more severe in proton detected NMR spectroscopy because disordered protein segments often sample multiple conformations on a time scale from micro- to milliseconds. One approach to minimize line-broadening is to alter the conformational exchange rate by changing the sample temperature; however, the improvement in the resulting spectrum is often limited under conditions close to physiological ones. Another challenge is that proton-detected NMR spectra are often severely overlapped because of the reduced complexity in amino acid sequences of IDPs and the small chemical shift dispersion in the proton dimension. Finally, rapid solvent exchange of the labile amide protons at physiologic pH and temperature can further contribute to line broadening and signal loss.

Together, sequence redundancies, limited spectral dispersion and unfavorable dynamic properties of IDPs can pose severe challenges for using standard proton-detected NMR techniques in the study of their roles in mediating protein interactions. Consequently, conventional proton-detected NMR spectra of IDPs/IDRs, such as $^1H$ $^{15}N$ HSQC, are often uninterpretable due to spectral overlap and/or line broadening. Thus, there is a need for improved NMR techniques to be able to probe the highly flexible regions of proteins and their roles in mediating protein-protein interactions.

SUMMARY

The present disclosure provides methods for determining the amino acids mediating the interaction between an intrinsically disordered region of a polypeptide and a macromolecule. In general, the methods comprise labeling the intrinsically disordered region of the polypeptide with $^{13}C$ and $^{15}N$, thereby producing a labeled polypeptide, interacting the labeled first polypeptide with a macromolecule, recording a $^{13}C$-detected nuclear magnetic resonance (NMR) spectrum of the labeled polypeptide interacted with the macromolecule, and detecting a decrease in intensity of, a loss of $^{13}CO$—$^{15}N$ peaks, or both intensity decrease and loss of $^{13}CO$—$^{15}N$ peaks in the recorded NMR spectrum relative to a reference NMR spectrum of the first polypeptide, thereby determining the amino acids that mediate the interaction between the intrinsically disordered region of the polypeptide and the macromolecule.

The polypeptide may comprise a protein, or a fragment thereof, of about 200 amino acids or less in length. The polypeptide may comprise an intrinsically disordered protein or a fragment thereof. The polypeptide may comprise a globular protein or a fragment thereof. The polypeptide may comprise one or more post-translational modifications. The polypeptide may comprise one or more of phosphorylations, acetylations, or methylations.

The macromolecule may comprise a biomolecule, such as a polypeptide or protein, or a nucleic acid such as DNA or RNA. In some embodiments, the macromolecule comprises an antibody or antigen-binding fragment thereof, such as an Fab, VH, VL, or VH and VL.

BRIEF DESCRIPTION OF THE DRAWINGS

FIG. 1A shows an exchange between two states, A and B, described by the rate constants in both directions, kA and kB, and chemical shifts of a given nucleus in each state, vA and vB. kex is the total exchange rate, kA+kB, and PA and PB are the population fractions of each state (PA+PB=1). FIG. 1B shows a schematic illustration of the effect of varying kex on NMR spectra, assuming PA=75% and Δv=100 Hz. Note that the time regime of chemical exchange is defined by the relative magnitudes of kex and Δv (each in units of Hz=s−1). In the slow exchange regime (kex«IΔv1), signals from both states are observed reflecting their distinct chemical shifts, intensities and linewidths. In the fast exchange regime (kex«IΔv1), only one signal is observed reflecting the population-weighted average of chemical shift, intensity and linewidth. In the intermediate exchange regime (kex≈IΔv1), only one signal is observed with intermediate chemical shift. Importantly, the linewidth is increased via "exchange broadening," which can sometimes render this signal undetectable. In each case, the linewidths reflect the local dynamics of the sites and the rate of their interconversion. (Adapted from Mittertnaier A K et al. (2009) Trends Biochem. Sci. 80:601).

FIGS. 2A-2C show NMR Spectra of NAurA recorded at 37° C. FIG. 2A shows the amino acid sequence of the N-terminal regulatory region of AurA, residues 1-131 MDRSKENICSGPVKATAPVGGPKRVLVTQQFPCQN-PLPVNSGQAQRVLCPSNSSQRIPL QAQKLVSSHK-PVQNQKQKQLQATSVPHPVSRPLNNTQKSKQPLPS-APENNPEELAASKQ KNEESKKRQWALE (SEQ ID NO:5); note that amino acids, K, L, N, P, Q, S, and V, comprise 69% of the sequence; FIG. 2B shows $^1$H—$^{15}$N HSQC of [$^{13}$C, $^{15}$N]-NAurA. Only about ⅔ of the expected peaks are observable; FIG. 2C shows the carbon-detected $^{13}$CO—$^{15}$N correlation (CON) spectrum. Most of the peaks, including those from proline residues, are well resolved. Sequence-specific assignments were obtained for 129 out of 131 residues in the CON spectrum.

FIG. 3A shows the CON spectrum of about 1 mM [$^{13}$C,$^{15}$N]-labeled NAurA in the absence (dark grey) and presence of 0.37 mM unlabeled apo-CaM (light grey). Binding of apo-CaM to NAurA caused a decrease in intensity or complete loss of $^{13}$CO—$^{15}$N peaks for residues involved in binding. FIG. 3B shows relative change in peak intensity for assigned cross peaks of NAurA at a concentration of 1 mM upon addition of apo-CaM to a final concentration of 0.18 mM (light grey) and 0.37 mM (dark grey). At an apo-CaM concentration of 0.18 mM, the peaks for residues 60-62 and 64 disappeared completely and the peak heights for a majority of the remaining residues within the 54-68 segment of NAurA decreased by more than 50%, indicating residues in the core of the binding site. After adding more apo-CaM to reach a molar fraction of 0.37 relative to NAurA, peak heights for residues 23-82 decrease further, indicating more peripheral regions of the binding interface.

FIGS. 4A through 4C show NMR Spectra of C-3DL1. FIG. 4A shows amino acid sequence of C-3DL1, residues 340-423 HLWCSNKKNAAVMDQEPAGNRTANSEDSD-EQDP EEVTYAQLDHCVFTQRKITRPSQRPKTPPTDTI-LYTELPNAKPRSKV (SEQ ID NO:6), with two potential SH2-domain binding motifs highlighted/underlined. The peptide VTYAQLD is SEQ ID NO:7 (not shown). The peptide ILYTEL is SEQ ID NO:8 (not shown). FIG. 4B shows $^1$H—$^{15}$N HSQC of [$^{13}$C—, $^{15}$N] C-3DL 1. Only ⅔ of the expected peaks arc observable; (C) carbon-detected $^{13}$CO—$^{15}$N correlation (CON) spectrum (dark: free, light: complex with molar ratio SHP-2-2SH2:C-3DL1:I:0.2). Most of the peaks, including those from proline residues, are well resolved. Sequence-specific assignments for 69 out of 84 residues are shown. Quantitative analysis showed that the first of the two putative SH2 binding motifs (EEVTYAQLD-HCVF (SEQ ID NO:4)) is the primary recognition site for the SHP-2 11 phosphatase. The peptide EEVTY is SEQ ID NO:3.

DETAILED DESCRIPTION

Figures 1A, 1B:
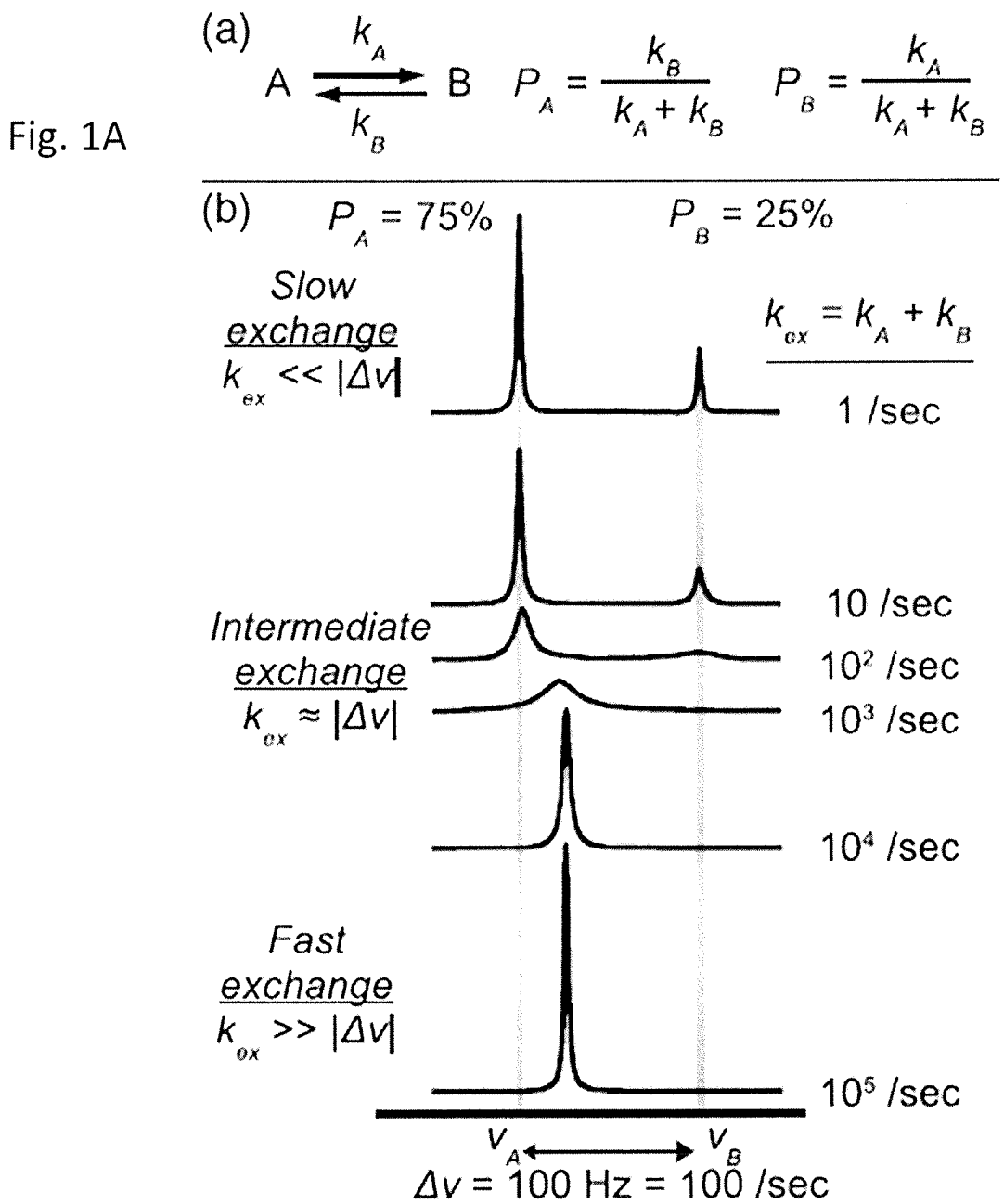
FIGS. 1A and 1B show the effect of conformational exchange on NMR spectra.

Various terms relating to aspects of the present disclosure are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

It was observed in accordance with the present disclosure that NMR methods based on direct detection of carbon are especially well suited for investigating interactions between globular proteins and intrinsically disordered proteins (IDP) or intrinsically disordered regions (IDR) of a protein. By recording a directly $^{13}$C-detected 2D NMR spectrum, using established techniques that measure the correlation between backbone $^{13}$CO and $^{15}$N groups, such as the simple CON or proton-start CON techniques, including (HCA)CON and (HN)CON, on a uniformly $^{13}$C and $^{15}$N-labeled IDR in the presence and absence of a interacting macromolecule (e.g., protein or nucleic acid), binding motifs on IDPs can be identified with single-residue resolution. It was further observed that the high-quality NMR spectra required for this protein footprinting technique can be obtained using standard, commercially available NMR equipment without the need for a specialized and expensive NMR probe optimized for carbon detection. All $^{13}$C-detected NMR spectra were recorded with a conventional triple-resonance cryogenic probe optimized for proton detection (Bruker TCI probe). Compared to proton detection methods, direct detection of carbon ($^{13}$C) signals is less sensitive, but can result in improved spectral resolution based on: (1) the frequency separation (Δv) between two carbon signals in different conformational stales is usually larger than that of the corresponding proton signals, thus, intermediate-exchange conditions in proton NMR can become slow-exchange conditions in carbon NMR, where the NMR signals from one of the states (unfolded/unbounded) will be sharper and more readily detectable (2) NMR signals from IDRs in the unfolded/unbounded state usually have much longer (5-10 fold) transverse (spin-spin) relaxation times ($T_2$) compared to those of fully ordered proteins. Because the line-width of an NMR signal is inversely related to $T_2$, NMR signals of IDPs/IDRs are much sharper and have higher intensity; and (3) the spectra are more resolved because of the relatively large carbonyl carbon chemical shift dispersion, even when the complexity in amino acid sequence is low.

To demonstrate effective characterization of the binding motifs in IDRs involved in interactions with another macromolecule, the studies assessed (1) the interaction between the disordered N-terminal domain of aurora kinase A (NAurA) and Calmodulin (CaM) and (2) the interaction between the C-terminal cytoplasmic domain of natural killer cell immunoglobulin-like receptor KIR-3DL I (C-3DL I) and two SH2 domains of Src-homology 2 domain-containing phosphatase 2 (SHP-2 2SH2, residues 1-246).

Prior studies have focused on resonance assignment for totally disordered proteins, which typically yield well-resolved NMR spectra with sharp lines not only in carbon-detected spectra, but also in conventional proton-detected spectra. It is believed there have been no previously described use of $^{13}C$ direct-detection methods for mapping protein-protein interactions where one of the binding partners is an IDP or IDR. Accordingly, the present disclosure provides methods for determining which amino acids mediate the interaction between an IDR or IDP and another macromolecule by using carbon NMR.

Once a polypeptide and biomolecule binding partner of interest are identified, a reference two dimensional carbon NMR spectrum of the polypeptide of interest, or at least the intrinsically disordered region thereof, is obtained. For example, a NMR spectrum may be recorded. The polypeptide of interest can be labeled with $^{13}C$ and $^{15}N$. Thus, in some embodiments, the recombinant polypeptide of interest is uniformly labeled with $^{13}C$ and $^{15}N$, and a $^{13}C$-detected $^{13}CO$—$^{15}N$ correlation (CON) spectrum is recorded. The $^{13}C$ and $^{15}N$ labeling may be achieved according to any suitable method. In some embodiments, labeling occurs by recombinant expression of the polypeptide by a suitable host cell, with the cell culture including $^{13}C$ and $^{15}N$.

Once the disordered region of the polypeptide is labeled, the labeled polypeptide is interacted with a biomolecule. During the interaction, a CON NMR spectrum of the labeled polypeptide interacted with the biomolecule is recorded. Following the recording of the NMR spectrum of the interaction, the decrease in intensity of, a loss of $^{13}CO$—$^{15}N$ peaks, or both the decrease in intensity and the loss of $^{13}CO$—$^{15}N$ peaks in the recorded NMR spectrum are detected. Such losses may be detected, for example, by comparison to a reference NMR spectrum of the first polypeptide not interacted with the biomolecule. From the loss of intensity and/or the loss of $^{13}CO$—$^{15}N$ peaks, the amino acids on the polypeptide that participate in the interaction with the biomolecule are thereby detected and a binding footprint is established for the intrinsically disordered region of the polypeptide and the biomolecule binding partner. Peak intensity may be determined at sub-stoichiometric concentrations of the biomolecule.

In some embodiments, the polypeptide of interest (that is labeled and whose binding residues are being queried) has about 200 amino acids or less (to a minimum of about 5 amino acids). The polypeptide may be a protein of about 200 or less amino acids in length (to a minimum of about 5 amino acids), or may be a fragment of a protein. The polypeptide may comprise an intrinsically disordered region. The polypeptide may comprise an intrinsically disordered protein, or a fragment thereof comprising amino acids of one or more intrinsically disordered regions of the protein. In some embodiments, the polypeptide comprises an epitope for an antibody that specifically binds to the polypeptide or region thereof.

In some embodiments, the polypeptide comprises one or more post-translational modifications. In some embodiments, the polypeptide is phosphorylated. In some embodiments, the polypeptide is acetylated. In some embodiments, the polypeptide is methylated.

The polypeptide may be substantially water-soluble. In some embodiments, the polypeptide has a solubility in an aqueous medium of at least about 0.5 mM. In some embodiments, the polypeptide is dissolved in an aqueous medium at a concentration of at least about 0.5 mM. In some embodiments, the IDP may be produced with attachment of a solubility-enhancement tag (SET) to its N-terminal to enhance solubility.

In some embodiments, the biomolecule is a known or queried binding partner to the polypeptide. The methods may be used to determine which amino acids in the polypeptide participate in the interaction with the biomolecule. The methods allow the determination of core regions of the interaction site on the polypeptide, as well as peripheral regions of the interaction site.

In some embodiments, the biomolecule comprises an enzyme. In some embodiments, the biomolecule comprises a second polypeptide, which may comprise a protein or portion thereof of any length. In some embodiments, the second polypeptide is not an intrinsically disordered polypeptide or protein.

In some embodiments, the biomolecule comprises an antibody. Thus, the footprinting methods may be used to determine the epitope of the antibody, e.g., epitope mapping, where the labeled/query polypeptide comprises an antigen of the antibody.

The biomolecule may comprise a nucleic acid. The nucleic acid may comprise DNA, RNA, or a combination thereof, or may comprise a complex of a nucleic acid and a polypeptide or protein. The nucleic acid may be single stranded, double stranded, or have multiple strands, and may comprise any conformation.

In some embodiments, the probe is a cryogenic probe. In some embodiments, the cryogenic probe has a high level of carbon sensitivity.

The following examples are provided to describe the present disclosure in greater detail. They are intended to illustrate, not to limit, the present disclosure.

EXAMPLES

Example 1: General Experimental Methods

Technical Requirements and General Procedures.

The NMR instrumentation was a Bruker Avance ≥600 MHz NMR spectrometer equipped with a triple-resonance cryoprobe (Bruker TCI cyroprobe, but a spectrometer and probe with equivalent or higher carbon sensitivity may be used). The mapping procedures for identifying binding motifs in IDRs are summarized as follows: (1) Prepare a DNA construct for a protein expression system of the soluble IDR to be studied by using standard molecular biology procedures. (2) According to standard protocols, express and purify uniformly-labeled sample of the IDR with the stable isotopes $^{13}$C and $^{15}$N, then prepare an NMR sample at a protein concentration of ~0.5 mM or higher in an appropriate buffer. (3) Record a proton detected $^1$H—$^{15}$N HSQC of the IDR as a reference. (4) Record direct carbon-detected CON spectrum. (5) Record a series of direct carbon-detected 3D NMR spectra, such as: C_CBCACON, C_CBCANCO, C_CCCON, C_CANCO, and C_CANCOi, for the sequential assignment of the main-chain $^{13}$CO—$^{15}$N cross peaks in the CON spectrum. (6) Record a $^{13}$C-detected 2D NMR spectrum, such as CON or (HCA)CON, of IDR in the absence of another macromolecule. (7) Record a 2D NMR spectrum under identical instrument and sample conditions for the IDR in the in the presence of increasing concentrations of its binding partner, which can be any soluble macromolecule (protein, monoclonal antibody or nucleic acid) without isotopic labeling. (8) Analyze the NMR data in terms of changes in chemical shifts and/or peak intensity due to addition of a binding partner to identify binding motifs.

Protein Expression and Purification.

NAurA DNA sequence encoding residues 1-131 was commercially synthesized (Life Technology, Thermo Fisher Scientific). The gene was subcloned into the expression vector pET49b (Novagen) between the BamH I and Hind III sites. An expression vector for chicken Calmodulin (CaM) was a gift. The gene encoding the cytoplasmic domain of KIR-3DL 1, including residues 340-423, was inserted into expression vector pET32b (Novagen) between the NcoI and BamH I sites. The gene of protein SHP-2, residues 1-247, was subcloned into pET49b between BamH I and Hind III sites. Each protein was purified from the *E. coli* Rosetta2 (DE3) or BLR(DE3) bacterial cells (Novagen), with corresponding expression systems. The cells were grown from LB media and protein expression was induced using standard protocols. Stable isotopic uniformly $^{13}$C and $^{15}$N labeled proteins were isolated from bacterial cells grown in M9 media supplement with $^{15}$N NH$_4$Cl (CIL) and $^{13}$C glucose (CIL). All proteins were purified using a 5 mL HisTrap column (GE Healthcare Life Sciences) according to the manufacturer's directions, except for CaM, which was purified with a hydrophobic column (phenyl-sepharose CL-4B, Sigma). The target proteins were cleavage from the fusion tag with HRV-3C protease (Novagen), except for C-3DL 1, which was cleavage by thrombin (BioPharm, Lab., LLC).

Nmr Spectroscopy.

NMR samples of uniformly $^{13}$C- and $^{15}$N-labeled NAurA or C-3DL 1 (~300 µl) were prepared by dissolving ~1 mM protein in buffer containing 20 mM HEPES, 20 mM NaCl, 3 mM EDTA, and 3 mM DTT, at pH 7.4 The purified protein contains a 33-amino acid SET attached at its N-terminus with a sequence of GSGMKETAAAKFERQHMDSPDLGT DDDDKAMEF (SEQ ID NO:2) to make the protein soluble. To form the complex of these IDRs with their respective binding partners, the samples were re-concentrated to a volume of ~300 µl after adding the desired amounts of target protein. All NMR spectra were recorded at 37° C. on a Bruker Avance II 600 MHz NMR instrument equipped with a TCI triple-resonance cryogenic probe. The data were acquired by using standard Bruker pulse sequences.

Example 2: Results

The Interaction Between NAur•A and CaM.

Figure 2B:
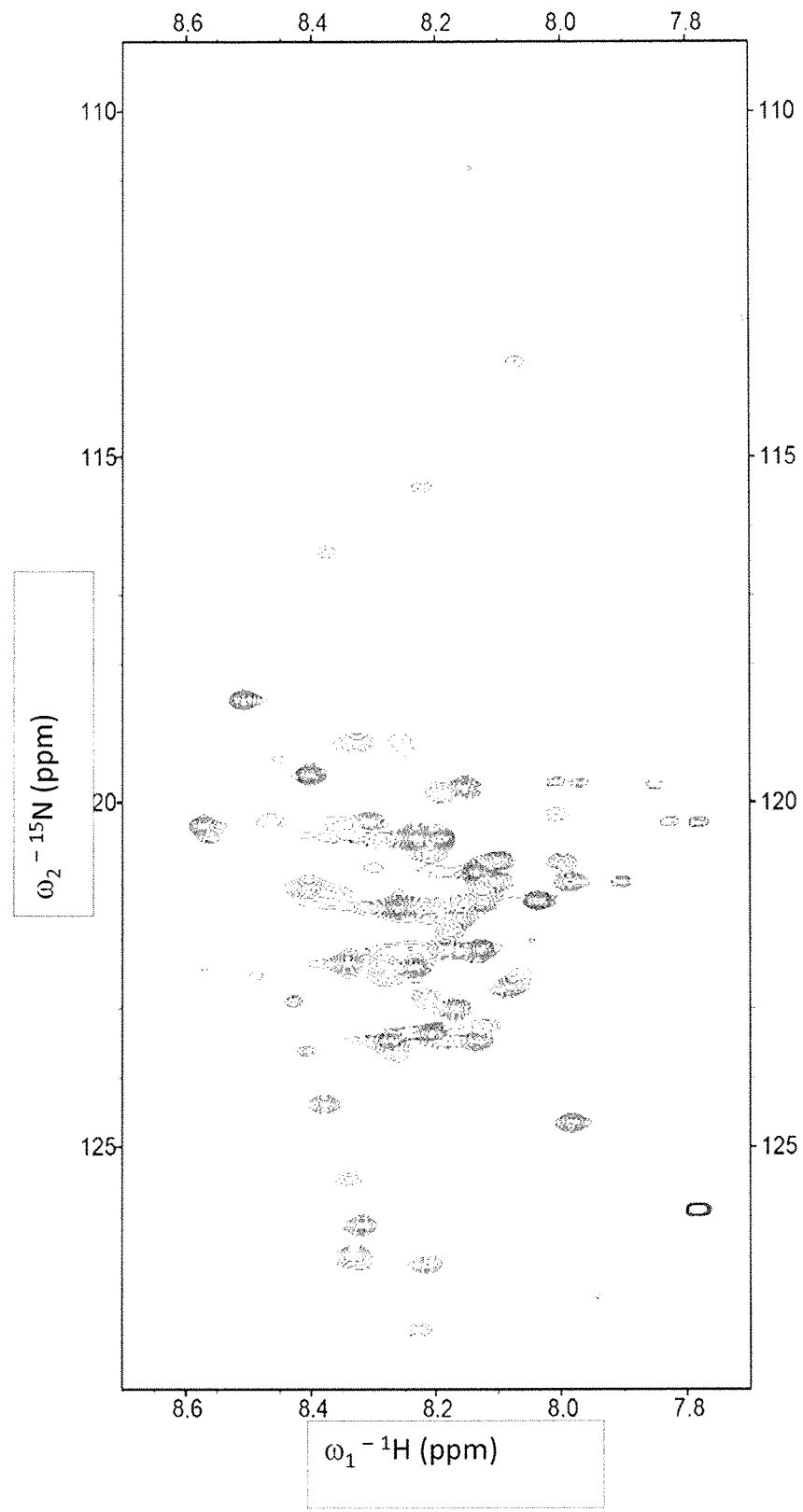

Purified NAurA is a 138 residue protein comprising residues 1-131 of AurA and an N-terminal GPGYQDP (SEQ ID NO:1) sequence after cleavage with HRV-3C protease. NAurA has low sequence complexity with seven amino acids (K, L, N, P, Q, S, and V) comprising 69% of the sequence (see, FIG. 2A). As shown in FIG. 2B, less than ⅔ of the expected peaks were resolved in the conventional proton detected $^1$H—$^{15}$N HSQC. The remaining peaks are either severely broadened due to conformational exchange or unresolved due to the redundancy in its sequence.

Figure 2C:
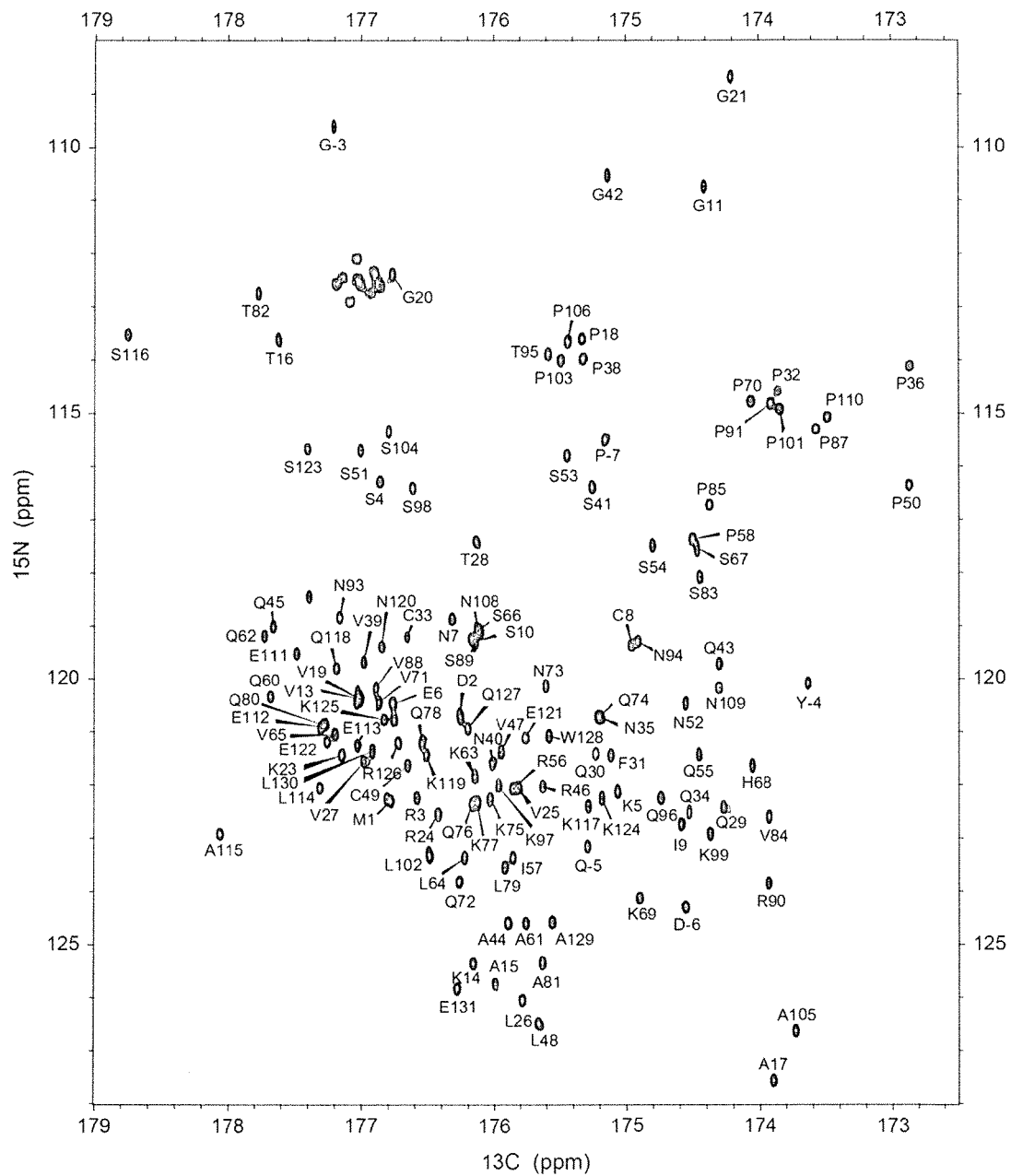

FIG. 2C shows the $^{13}$C-detected $^{13}$CO—$^{15}$N correlation (CON) spectrum. Most of the peaks, including those from proline residues, are well-resolved. The large chemical shift range in the carbon dimension minimizes line broadening due to conformational exchange and signal overlap despite its highly redundant sequence. Using various multidimensional NMR experiments, all involving direct detection of $^{13}$C signals, sequence-specific assignments were obtained for the backbone carbons and nitrogens of 129 out of 131 residues as well as most of their side chain carbons.

Figure 3A:
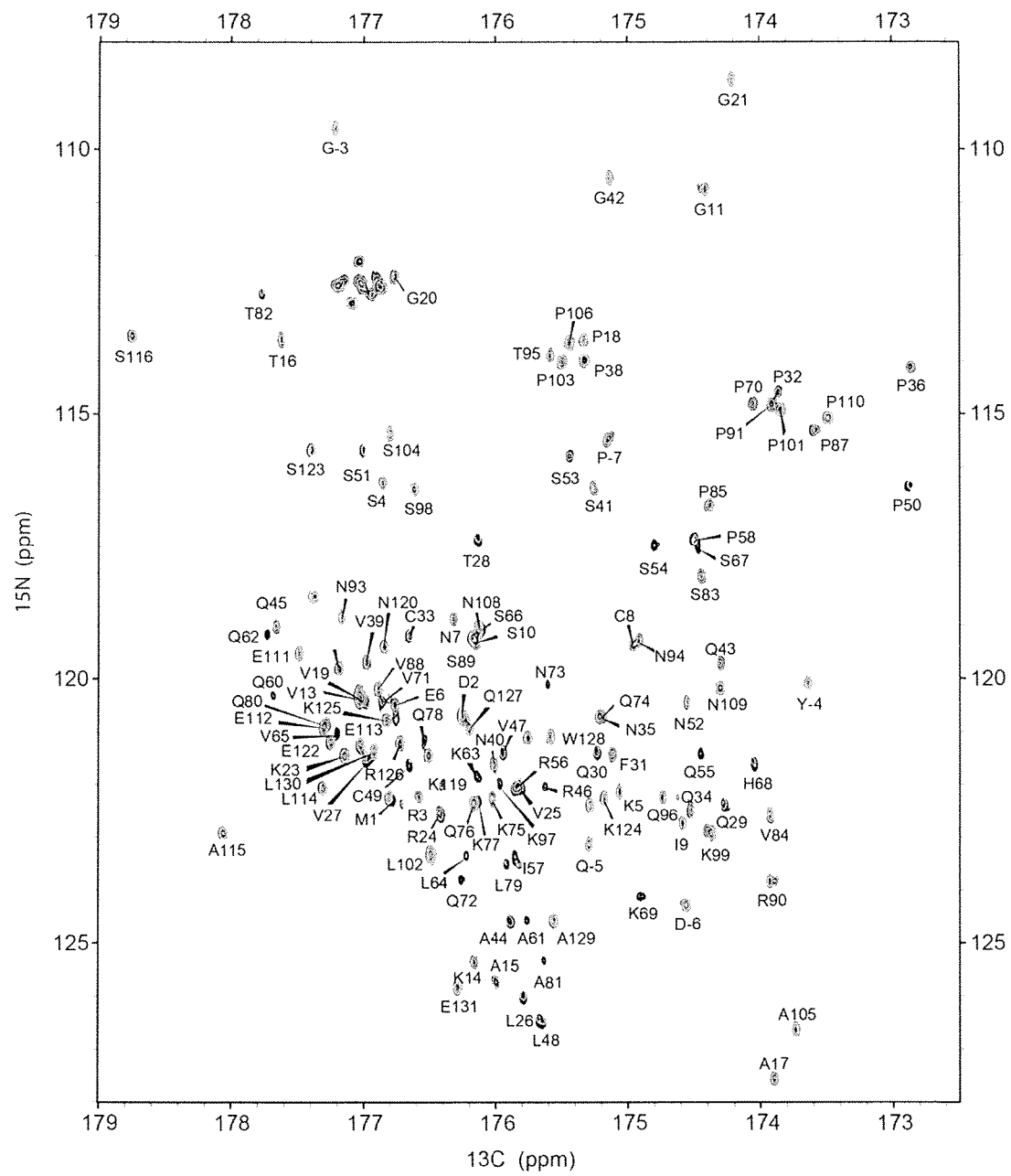
FIGS. 3A and 3B show the interaction between NAurA and apo-CaM.
Figure 3B:
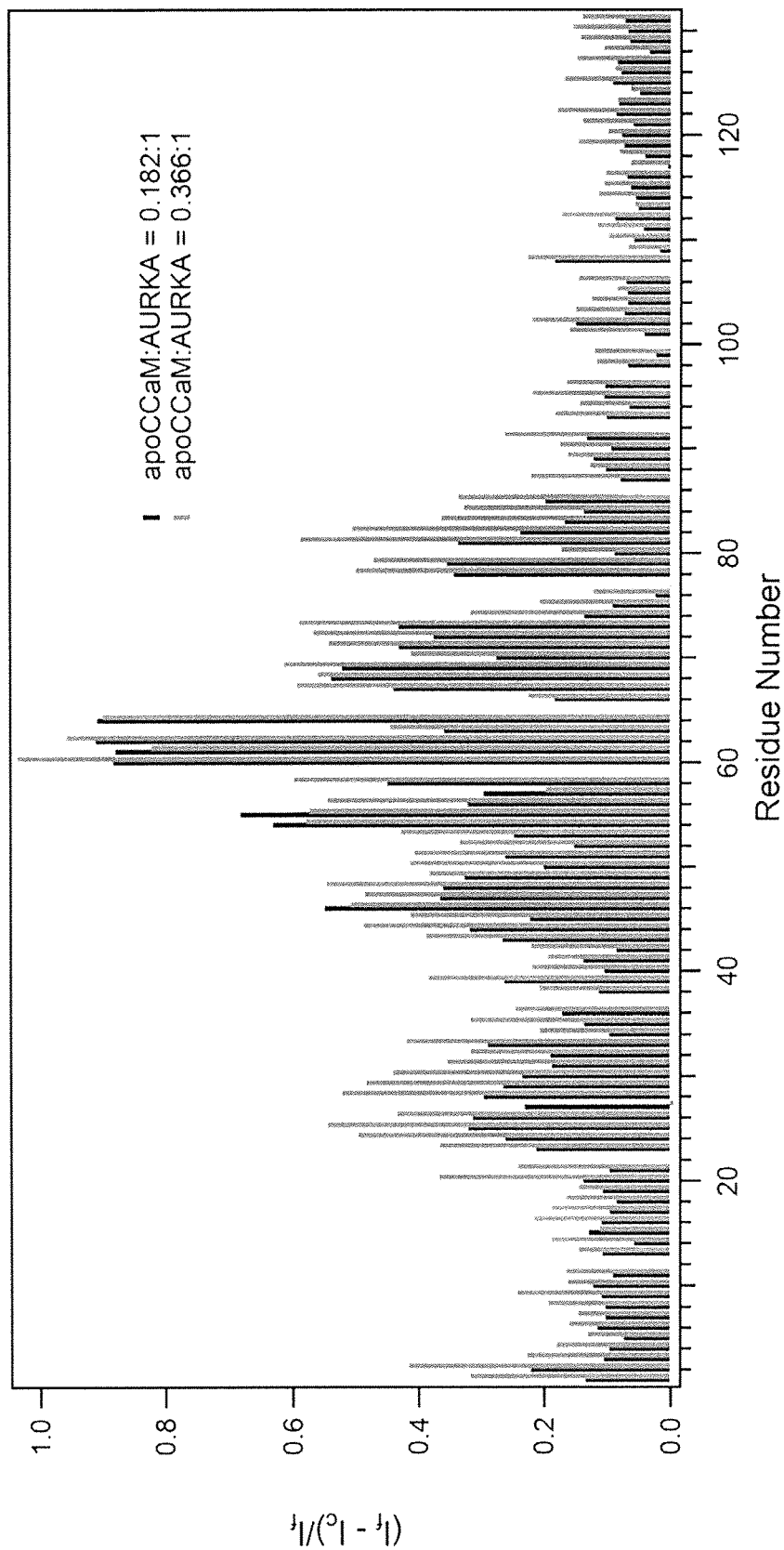

It was previously shown that CaM binds with high affinity to AurK, by recognizing a binding site in the 33-89 region of NAurA. Addition of unlabeled calcium-free CaM (apo-CaM) to an NMR sample of isotopically labeled NAurA caused a decrease in intensity or complete loss of $^{13}$CO—$^{15}$N peaks for residues involved in binding. In a first experiment, when the molar ratio of apo-CaM to NAurA was 0.18 to 1, the peaks for residues 60-62 and 64 disappeared completely and the peak heights for a majority of the remaining residues within the 54-68 segment of NAurA decreased by more than 50% (see, FIG. 3A), indicating these residues are at the core of the binding site. After adding more apo-CaM to reach a molar fraction of 0.37 relative to NAmA, further reduction in peak height was observed for residues 23-82, indicating more peripheral regions of the binding interface (see, FIG. 3B). These results are consistent with previous cell-biological data, but provide more detailed structure information in terms of individual residues of NAurA that are recognized by CaM.

Interaction Between C-3DLI and SHP-2 2SH2.

The disordered C-terminal region of KIR-3DL 1 (C-3DL1) contains 84 amino acids. After thrombin cleavage, purified C-3DL1 is a 117 residue-protein with 33 addition amino acids at the N-terminus (GSGMKETAAAKFERQH MDSPDLGTDDDDKAMEF) (SEQ ID NO:2). Previous sequence analysis and cell biological studies identified two potential SH2-domain binding motifs centered on the two tyrosine residues in the sequence of C-3DL1 (see, FIG. 4A). Direct carbon detection NMR techniques were used to determine whether the SH2-domain of SHP-2 preferentially binds to one of these motifs when C-3DL1 is unphosphorylated.

Figure 4B:
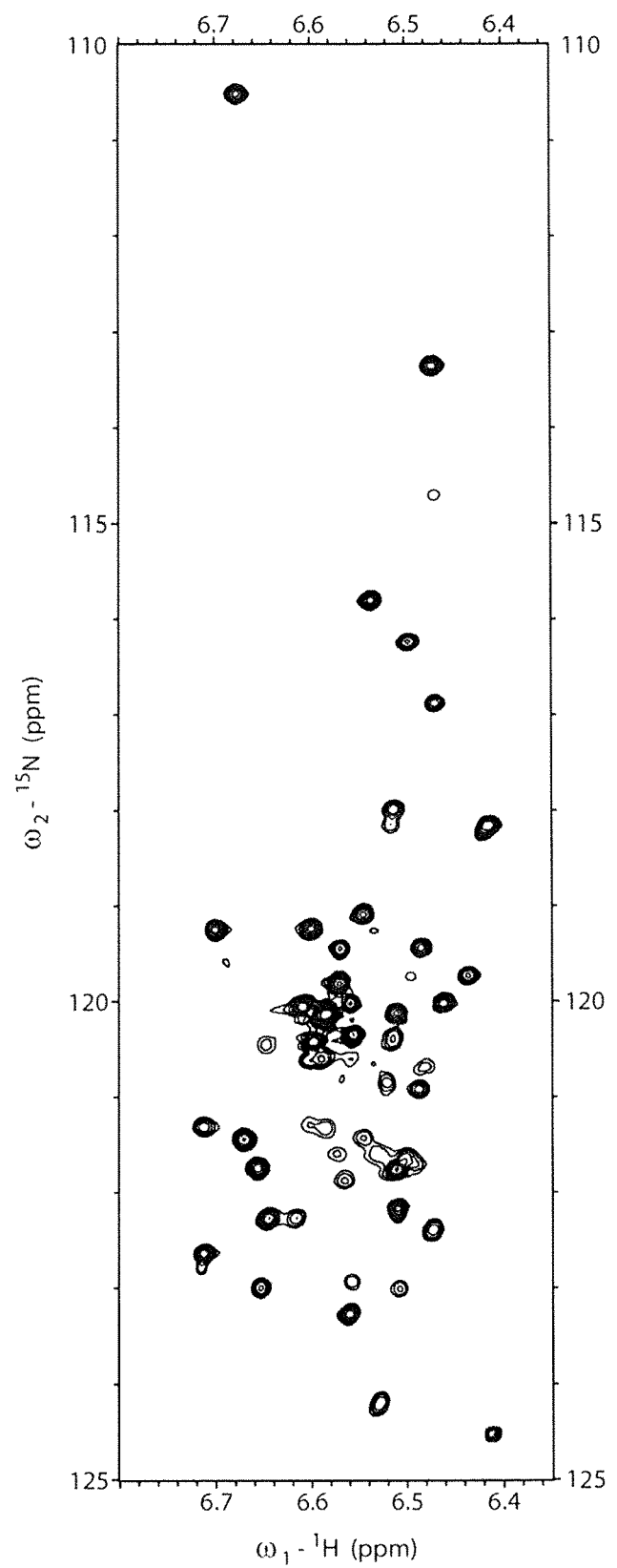
Figure 4C:
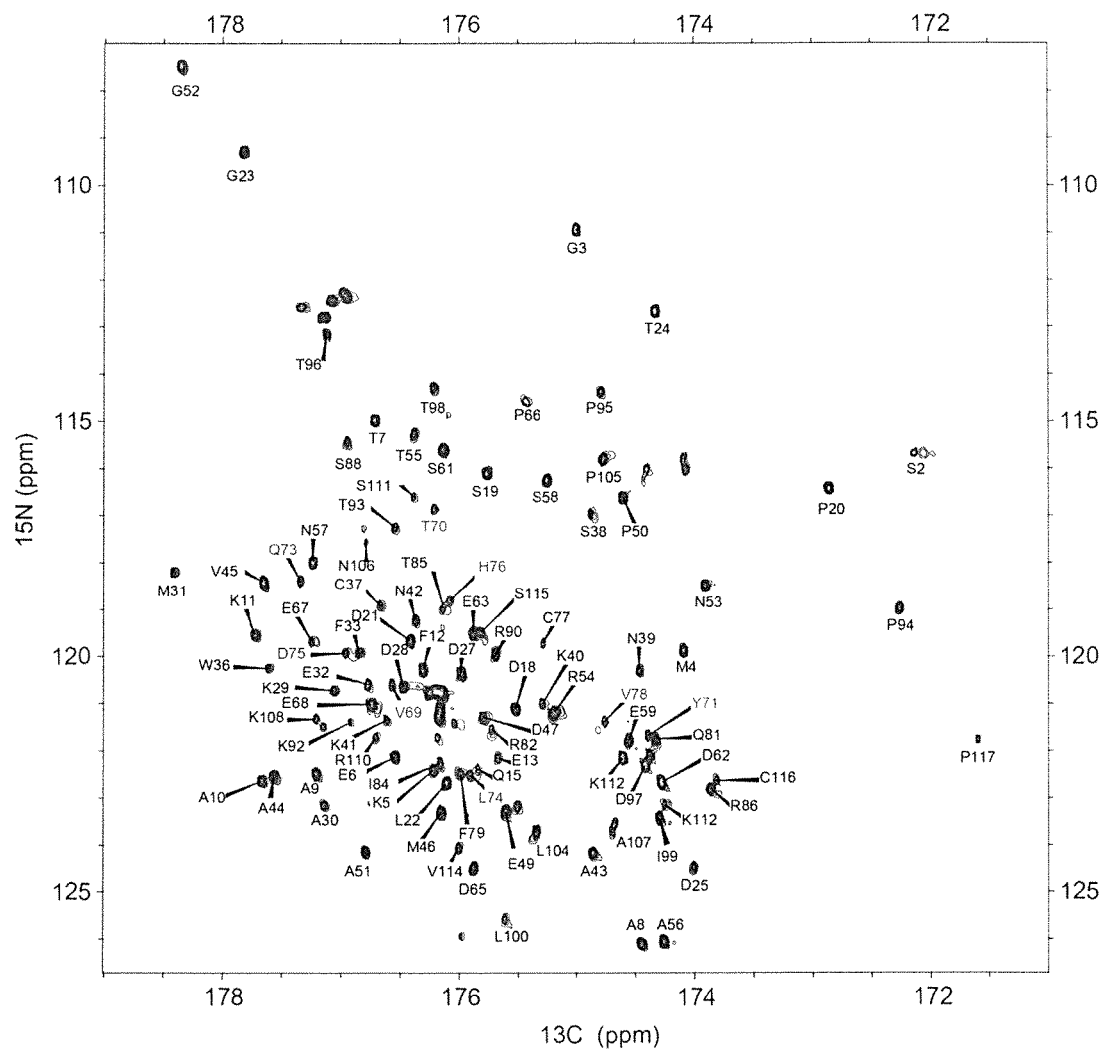

FIG. 4B (dark grey) shows the conventional proton detected $^1$H—$^{15}$N HSQC spectrum for C-3DL 1. Although the peaks were sharper than those of NAurA, less than 60% of the expected peaks are resolved; the remaining peaks are either broad due to the conformational exchange or unresolved due to the small proton chemical shift range. In contrast, almost all peaks (including Pro residues) are well resolved in the carbon detected CON spectrum, which minimizes line broadening and signal overlap. After assigning 69 out of 84 residues, the interaction between C-3DL 1 and SH2 domains of SHP-2 was studied by adding purified SHP-2 2SH2 (unlabeled) to the $^{13}$C/$^{15}$N-labeled C-3DL1 sample. FIG. 4C shows the CON spectrum C-3DL 1 in the presence of SHP-2 2SH2 at a molar fraction of 20% (light grey) superimposed on the CON of free C-3DL1 (dark grey). Most of the cross peaks assigned to residues 36-45 are weak or absent in the spectrum of the complex. Quantitative analysis of the changes in peak heights showed that a majority of residues between 33 and 46 experience a decrease in peak intensity of at least 50% (see, FIG. 4C). This region contains the first of the two putative SH2 binding motifs (EEVTYAQLDHCVF (SEQ ID NO:4)), which is thus identified as the primary recognition site for the SHP-2 phosphatase.

Example 3: Summary

Initial applications of the carbon NMR footprinting technique to two different systems: (I) the interaction between the disordered N-terminal domain of aurora kinase A (NAurA) and Calmodulin (CaM); (2) the interaction between the C-terminal cytoplasmic domain of a natural killer cell immunoglobulin-like receptor (C-3DL 1) and the SH2 domains of a tyrosine-protein phosphatase (SHP-2 2SH2), allowed the identification of the specific residues in intrinsically disordered protein regions (IDRs) involved in recognizing an interacting protein. The data show that direct carbon detection NMR techniques are a powerful tool for characterizing the interaction between globular proteins or domains and IDRs despite the fact that the latter are highly dynamic and do not adopt a unique structure. Conformational dynamics on a micro- to millisecond time scale often makes $^1$H conventional proton-detected NMR spectra uninterpretable. Direct carbon detection methods result in multi-dimensional NMR spectra with dramatically reduced line broadening and can be fully resolved and specifically assigned even for proteins with low sequence complexity. The favorable relaxation properties of carbon nuclei of IDRs make it possible to collect NMR data by using a standard proton-optimized cryoprobe. Upon addition of an unlabeled globular protein to an NMR sample of an isotopically labeled IDR, the binding site can be mapped to specific residues on the IDR by following the changes in intensity for $^{13}$CO—$^{15}$N cross peaks at sub-stoichiometric concentrations of the binding partner. Compared to conventional biochemical and cell-biological techniques, the advantages of this carbon NMR protein footprinting method include (1) allowing mapping of protein interactions with single-reside resolution, and (2) differential effects on peak intensity allow identification of core vs. peripheral regions of the binding site.

Given that protein-protein interactions involving disordered regions of proteins are a ubiquitous feature of cell signaling and other biological systems, it is believed that the technique introduced here will become an important tool for studies of macromolecular interaction networks. Another application of major practical importance in biotechnology and biomedical research is to map epitopes for antibodies recognizing IDRs or IDPs, which includes monoclonal antibodies used in molecular and cellular biology as well as therapeutic antibodies. In addition, the methods can be used to study protein posttranslational modifications, such as phosphorylation, methylation and acetylation. Real-time studies of the kinetics of modification are believed to be possible by using a cryogenic probe with higher carbon sensitivity (such as the Bruker DCH, which has a ≥2-folcl higher carbon sensitivity than a conventional TC1 probe).

The present disclosure is not limited to the embodiments described and exemplified above, but is capable of variation and modification within the scope of the appended claims.

What is claimed is:

1. A method for determining the amino acids mediating an interaction between an intrinsically disordered region of a first polypeptide and a biomolecule, comprising:
    labeling the intrinsically disordered region of the first polypeptide with C and N, thereby producing a labeled first polypeptide;
    interacting the labeled first polypeptide with the biomolecule;
    recording a nuclear magnetic resonance (NMR) spectrum of the labeled first polypeptide interacted with the biomolecule;
    detecting the decrease in intensity of, a loss of $^{13}CO$—$^{15}N$ peaks, or both the decrease in intensity and the loss of $^{13}CO$—$^{15}N$ peaks in the recorded NMR spectrum relative to a reference NMR spectrum of the first polypeptide, and
    from the loss of intensity and/or the loss of $^{13}CO$—$^{15}N$ peaks, the amino acids on the first polypeptide that participate in the interaction with the biomolecule are thereby detected and a binding footprint is established for the intrinsically disordered region of the first polypeptide and the biomolecule.

2. The method according to claim 1, wherein the first polypeptide is a protein of about 200 amino acids or less in length.

3. The method according to claim 1, wherein the first polypeptide is an intrinsically disordered protein of about 200 amino acids or less in length.

4. The method according to claim 1, wherein the first polypeptide is phosphorylated.

5. The method according to claim 1, wherein the first polypeptide is acetylated.

6. The method according to claim 1, wherein the first polypeptide is methylated.

7. The method according to claim 1, wherein the first polypeptide comprises a post-translational modification.

8. The method according to claim 1, wherein the first polypeptide has a solubility in an aqueous medium of at least 0.5 mM.

9. The method according to claim 1, wherein the biomolecule comprises a second polypeptide that is not intrinsically disordered.

10. The method according to claim 9, wherein the second polypeptide is a protein.

11. The method according to claim 1, wherein the second polypeptide comprises an antibody.

12. The method according to claim 1, wherein the biomolecule comprises a nucleic acid.

13. The method according to claim 12, wherein the nucleic acid comprises DNA.

14. The method according to claim 12, wherein the biomolecule comprises a protein-nucleic acid complex.

15. The method according to claim 1, wherein the step of recording a nuclear magnetic resonance (NMR) spectrum of the labeled first polypeptide interacted with the second polypeptide is carried out using an NMR spectrometer equipped with a cryogenic probe having a high level of carbon sensitivity.

* * * * *